(12) United States Patent
Asirvatham et al.

(10) Patent No.: US 10,137,229 B2
(45) Date of Patent: Nov. 27, 2018

(54) TREATING CONGESTIVE HEART FAILURE

(75) Inventors: Samuel J. Asirvatham, Rochester, MN (US); Soon J. Park, Rochester, MN (US); Paul A. Friedman, Rochester, MN (US); Charles J. Bruce, Rochester, MN (US); Sudhir S. Kushwaha, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 748 days.

(21) Appl. No.: 13/319,672

(22) PCT Filed: May 11, 2010

(86) PCT No.: PCT/US2010/034389
§ 371 (c)(1),
(2), (4) Date: Nov. 9, 2011

(87) PCT Pub. No.: WO2010/132451
PCT Pub. Date: Nov. 18, 2010

(65) Prior Publication Data
US 2012/0059459 A1 Mar. 8, 2012

Related U.S. Application Data

(60) Provisional application No. 61/177,075, filed on May 11, 2009.

(51) Int. Cl.
*A61M 1/10* (2006.01)
*A61N 1/362* (2006.01)
(Continued)

(52) U.S. Cl.
CPC ............ *A61M 1/10* (2013.01); *A61M 1/1039* (2014.02); *A61M 1/101* (2013.01); *A61M 1/1005* (2014.02);
(Continued)

(58) Field of Classification Search
CPC .................................. A61F 2/82; A61M 1/10
(Continued)

(56) References Cited

U.S. PATENT DOCUMENTS 4,302,854 A * 12/1981 Runge .......................... 623/3.11
4,753,221 A    6/1988 Kensey et al.
(Continued)

FOREIGN PATENT DOCUMENTS

| EP | 0445782 | 9/1991 |
| WO | WO2008/02471 | 1/2008 |
| WO | WO 2008/027869 | 3/2008 |

OTHER PUBLICATIONS

International Preliminary Report on Patentability in International Application No. PCT/US2010/034389, dated Nov. 15, 2011, 7 pages.

(Continued)

*Primary Examiner* — Matthew Schall
(74) *Attorney, Agent, or Firm* — Fish & Richardson P.C.

(57) ABSTRACT

This document relates to materials and methods for circulatory bypass of a ventricle in the heart of a mammal. For example, materials and methods for bypassing a permanently or temporarily impaired left ventricle in the heart of a mammal (e.g., a human) are provided.

32 Claims, 11 Drawing Sheets

(51) Int. Cl.
*A61N 1/39* (2006.01)
*A61M 1/12* (2006.01)
(52) U.S. Cl.
CPC ......... *A61M 1/1008* (2014.02); *A61M 1/1034* (2014.02); *A61M 1/1086* (2013.01); *A61M 1/122* (2014.02); *A61M 1/125* (2014.02); *A61M 2205/33* (2013.01); *A61M 2205/3303* (2013.01); *A61N 1/3627* (2013.01); *A61N 1/3962* (2013.01)
(58) Field of Classification Search
USPC .......................................... 623/2.1, 3.1, 3.11
See application file for complete search history.

(56) References Cited

U.S. PATENT DOCUMENTS

| | | | |
|---|---|---|---|
| 4,919,647 A | 4/1990 | Nash | |
| 5,693,091 A * | 12/1997 | Larson et al. | 623/3.27 |
| 6,123,724 A * | 9/2000 | Denker | 623/3.11 |
| 6,136,025 A | 10/2000 | Barbut et al. | |
| 6,533,716 B1 | 3/2003 | Schmitz-Rode et al. | |
| 6,926,662 B1 | 8/2005 | Aboul-Hosn et al. | |
| 7,229,402 B2 * | 6/2007 | Diaz | A61M 1/1037 600/16 |
| 9,314,556 B2 | 4/2016 | Tuseth | |
| 2005/0187425 A1 | 8/2005 | Alferness et al. | |
| 2005/0228212 A1 * | 10/2005 | Aboul-Hosn | A61F 2/82 600/16 |
| 2006/0161095 A1 | 7/2006 | Aboul-Hosn et al. | |
| 2006/0181843 A1 | 8/2006 | Takahashi | |
| 2007/0156010 A1 | 7/2007 | Aboul-Hosn | |

OTHER PUBLICATIONS

International Search Report and Written Opinion in International Application No. PCT/US2010/034389, dated Dec. 20, 2010, 11 pages.

European Office Action in Application No. EP10775405.3, dated Jul. 4, 2017, 5 pages.

* cited by examiner

TREATING CONGESTIVE HEART FAILURE

CROSS-REFERENCE TO RELATED APPLICATIONS

This application is a National Stage application under 35 U.S.C. § 371 and claims benefit under 35 U.S.C. § 119(a) of International Application No. PCT/US2010/034389, having an International Filing Date of May 11, 2010, which claims benefit to U.S. Provisional Application Ser. No. 61/177,075, fled May 11, 2009. The disclosures of the prior applications are considered part of (and are incorporated by reference in) the disclosure of this application.

BACKGROUND

1. Technical Field

This document relates to materials and methods for circulatory bypass of a ventricle in the heart of a mammal. For example, materials and methods for bypassing a permanently or temporarily impaired left ventricle in the heart of a mammal (e.g., a human) are provided.

2. Background Information

Congestive heart failure (CHF) affects the ability of the heart to provide sufficient blood flow to the organs of the body. Conditions such as coronary artery disease, scar tissue from a myocardial infarction, high blood pressure, and heart valve disease can contribute to congestive heart failure. Pharmaceutical intervention can expand blood vessels and/or or lower blood pressure to allow blood to flow more easily and the heart to pump more efficiently. If the damage to the heart is extensive, surgical intervention can be required.

SUMMARY

This document relates to materials and methods for circulatory bypass of a ventricle in the heart of a mammal. For example, materials and methods for bypassing a permanently or temporarily impaired left ventricle in the heart of a mammal (e.g., a human) are provided. In some cases, the devices provided herein can be used as percutaneous assist devices for enhancing blood flow from a failing heart (e.g., a heart with a failing left ventricle or valvular disease). In some cases, the methods provided herein can be used to position an assist device within the heart of a mammal (e.g., within the shared wall of the aorta and left atrium of a human heart). Assist devices provided herein can be configured to reduce the risk of thrombosis and conform to the anatomy of a recipient without causing damage to the heart itself.

In addition, this document relates to materials and methods for treating various heart conditions. For example, assist devices provided herein can be used to support the function of a heart to treat congestive heart failure (e.g., left, right, and bilateral failure), cardiac arrhythmias (e.g., tachycardia and fibrillations), diastolic dysfunction, or valve disease (e.g., aortic and/or mitral valve stenosis). In some cases, an assist device can be configured to provide phasic flow to coordinate device activity with the natural rhythm of a heart. For example, sensing and/or pacing electrodes can be implanted with an assist device to time blood flow. An assist device provided herein can be used to replace or support other cardiac technologies (e.g., defibrillators or pacemakers). In some cases, assist devices can be combined to provide a complete heart system (e.g., left ventricular and right ventricular assist devices), which can be used to replace a failing heart. In some cases, assist devices provided herein can be used to bypass an impaired heart and to sustain circulation in a patient with end-stage heart failure until a donor heart or an artificial heart can be implanted (e.g., as a bridge to transplant).

In general, one aspect of this document features a ventricular assist device for improving blood flow in a mammal. The ventricular assist device comprises, or consists essentially of, a conduit and a pump. The conduit can include a proximal region, a distal region and an intermediate region located between the proximal and distal regions. The proximal region can be adapted to be positioned within a first compartment in the cardiovascular system of the mammal, and the distal region can be adapted to be positioned within a second compartment in the cardiovascular system. The intermediate region can define a lumen through a wall between the first and second compartments. The pump can be adapted to be positioned within the conduit. The mammal can be a human. The conduit can be constructed of expandable or malleable material. The malleable material can be nitinol. The proximal region and the distal region can be independently adjustable. The intermediate region can comprise a tubular core. The tubular core can comprise a septum or valve. The first compartment can be the aorta and the second compartment can be the left atrium. The ventricular assist device can comprise electrodes.

In another aspect, this document features a method for treating heart disease in a mammal. The method comprises, or consists essentially of, implanting an assist device within the cardiovascular system of the mammal, under conditions wherein blood flow in the mammal is enhanced, thereby treating the heart disease. The assist device can comprise, or consist essentially of, a conduit, and a pump. The conduit can comprise a proximal region, a distal region and an intermediate region located between the proximal and distal regions. The proximal region can be adapted to be positioned within a first compartment in the cardiovascular system of the mammal, and the distal region can be adapted to be positioned within a second compartment in the cardiovascular system. The intermediate region can define a lumen through a wall between the first and second compartments. The pump can be adapted to be positioned within the conduit. The method can include identifying the mammal as having a heart disease selected from the group consisting of congestive heart failure, valvular disease, and malignant cardiac arrhythmia. The mammal can be a human. The implanting step can comprise inserting the conduit into a shared wall between the aorta and the left atrium of the mammal. The conduit can be constructed of expandable or malleable material. The malleable material can be nitinol. The proximal region and the distal region can be independently adjustable. The intermediate region can comprise a tubular core. The tubular core can comprise a septum or valve. The first compartment can be the aorta and the second compartment can be the left atrium. The ventricular assist device can include electrodes.

In another aspect, this document features a method for implanting an assist device into a human. The method comprises, or consists essentially of, inserting a conduit having a proximal region, a distal region, and an intermediate region located between the proximal and distal regions into a position wherein the proximal region is located within the aorta of the human, the distal region is located within the left atrium of the human, and the intermediate region defines a lumen through the shared wall between the aorta and left atrium, and inserting a pump into the conduit such that blood is pumped through the conduit from the left atrium to the aorta.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
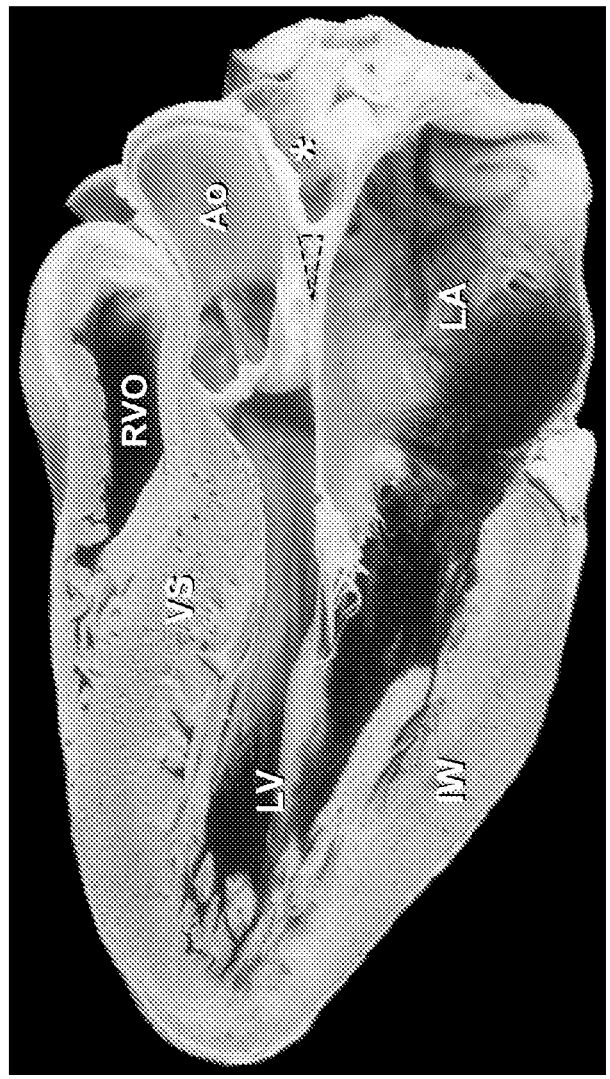
FIG. 1 is a photograph of a cross-section of a heart (Ao=Aorta, RVO=Right Ventricular Outflow, LV=Left Ventricle, LA=Left Atrium, VS=Ventricular Septum, IW=Intraventricular Wall, * dashed triangle=LV/Ao shared wall).

This document relates to materials and methods for circulatory bypass of a ventricle in the heart of a mammal. For example, materials and methods for bypassing a permanently or temporarily impaired left ventricle in the heart of a mammal (e.g., a human) are provided. Referring to FIG. 1, a heart is a muscular organ responsible for pumping blood in the body of a mammal. A healthy heart functions by collecting de-oxygenated blood from the body in the right atrium and pumping it, via the right ventricle outlet (LVO), into the lungs to be re-oxygenated. The left side of the heart collects oxygenated blood from the lungs into the left atrium (LA). Blood moves from the left atrium, to the left ventricle (LV), which pumps it out to the body via the aorta (Ao). In most hearts, there is direct continuity (i.e., a shared wall) between the left atrium and coronary cusp of the aorta.

Figure 2:
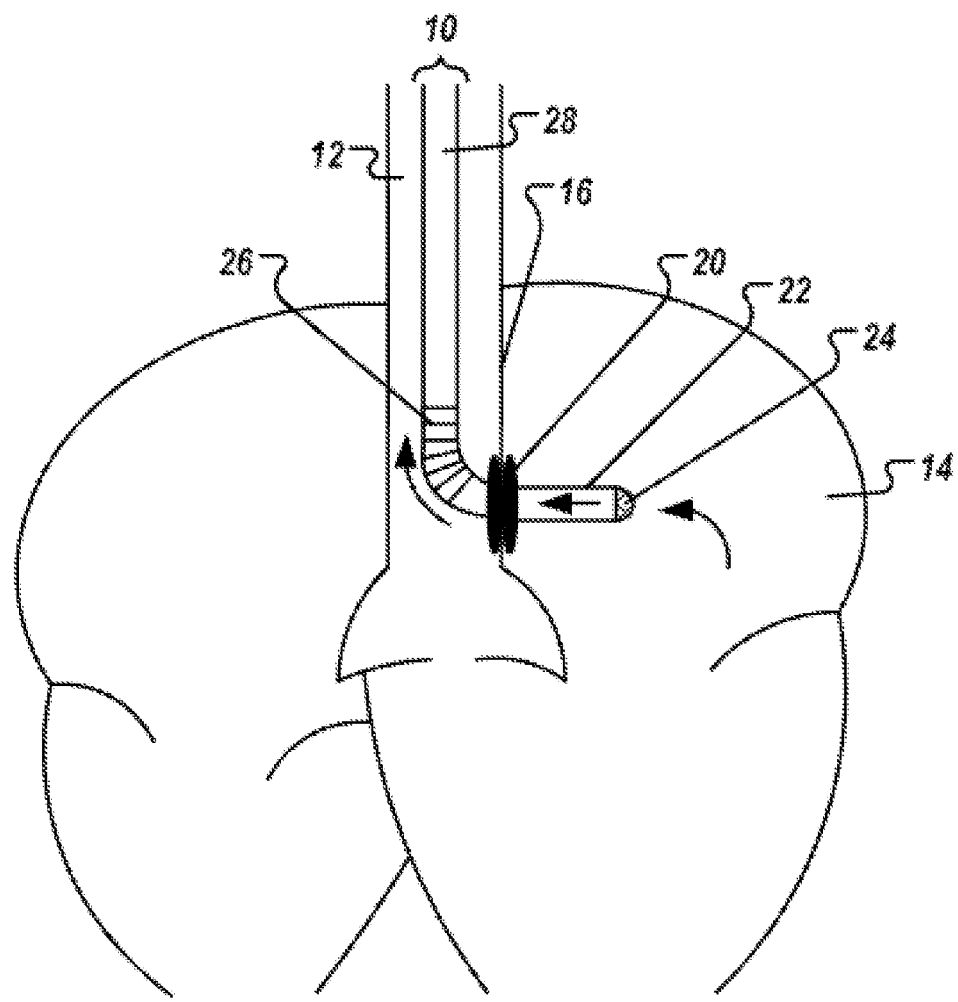
FIG. 2 is a diagram of an assist device positioned in a heart. Arrows show the direction of the flow of blood due to mechanical pumping (MV=Mitral Valve, TV=Tricuspid Valve, AV=Aortic Valve).

Blood flow can be enhanced mechanically using assist devices described herein. As shown in FIG. 2, an assist device 10 can be positioned within two compartments of the cardiovascular system. For example, an assist device can enhance the flow of blood to a first compartment, such as the aorta 12, from a second compartment, such as the left atrium 14, via a puncture in a shared wall 16 of the two compartments. A percutaneous assist device can include a conduit 20. A conduit can facilitate placement of a pump 22 to enhance blood flow. For example, a pump can transport blood from the left atrium to the aorta via a pump inflow 24 located in the left atrium and a pump outflow 26 located in the aorta. The pump can be manipulated into position in the cardiovascular system via a delivery element 28 that functions to place and then secure the pump in position between the left atrium and ascending aorta, for example.

An assist device described herein can enhance the flow of blood between any first compartment and second compartment in the cardiovascular system of a mammal. For example, a compartment can be any chamber of the heart or any blood vessel in the heart or the peripheral circulation. A first and second compartment can be in close apposition. In some cases, a first and second compartment can share a common wall (e.g., the aorta and the left atrium).

A pump of an assist device can be any type of blood pump for insertion into the cardiovascular system of a mammal including, without limitation, a positive displacement pump, a roller pump, a centrifugal pump, an impeller pump, an axial flow pump, a pulsatile pump, a magnetic flux pump, and a continuous-flow pump. (See, e.g., pumps and assist devices described in U.S. Pat. Nos. 4,919,647 and 4,753,221; U.S. Pat. Pub. Nos. 2005/0187425, 2007/0156010, and 2006/0181843). Suitable pumps can be inserted and secured into position and later removed or replaced, as necessary. In some cases, pumps can be pre-fitted on a delivery element and configured for specific anatomic locations. For example, a pump can be designed with any length required for an ultimate anatomic destination. A pump for placement between the left atrium and ascending aorta can have a relatively short length, for example. In some cases, an assist device can have more than one pump (e.g., multiple pumps connected in series). For example, a first pump can be positioned between the left atrium and ascending aorta, and include a second pump placed between the right atrial appendage and the pulmonary trunk that is connected to the first pump.

A pump can be designed to pass through a conduit. For example, a pump can be adapted so that one end of the pump (e.g., the inflow) can be positioned near one end of a conduit (e.g., near the distal end) and the other end of the pump (e.g., the outflow) can be positioned near the other end of a conduit (e.g., the proximal end). In some cases, the distance between a pump's inflow and outflow can be relatively short (e.g., the thickness of the shared wall between the left atrium and the ascending aorta). In some cases, a pump can be designed so that the pump motor and/or power supply can be located outside the conduit (e.g., for implantation subcutaneously in a mammal's infraclavicular, pectoral, or abdominal region).

A pump can be adapted to reduce the risk of thrombus formation. In some cases, a pump can be designed to minimize contact between the blood and the pump components, thereby presenting a limited risk of hemolysis and thrombus formation (e.g., by shortening the length of components). In some cases, a pump can feature a diverting element (e.g., a funnel-like shelf) that directs blood flow backwards onto the pump itself. For example, an assist device can be adapted to minimize ventricular stasis and the risk of thrombus formation by providing side ports or irrigation ports to the pump at the atrial end of the pump (i.e., inflow). Side ports or irrigation ports can divert blood flow to irrigate the pump itself, thereby preventing stasis and thrombus formation. In some cases, a pump can feature a combination of side ports, irrigation ports, and diverting elements.

The configuration of side ports or irrigation ports in a pump can depend on the anatomical destination of the pump or the surgical approach used to position the pump. For example, sections of the pump that are in contact with a left-sided circulation can feature multiple irrigation ports (e.g., a pump that will bridge the Fossa Ovalis to the aorta or a transaortic pump). In some cases, a pump that can be implanted using a retrograde approach can have a lengthy portion featuring numerous side ports or irrigation ports. Inflow at side ports facing the mitral valve can create a circulation-like effect. A side port can be extended to the left atrial appendage or in the direction of the left atrial appendage to prevent stasis in the left atrial appendage. An extended side port can be placed across the atrio-ventricular valve, or just atrial to the atrio-ventricular valve, to function as an inflow or intermittent outflow port. In some cases, a pump can be configured to reverse the direction of flow from a side port on regular intervals (e.g., every about 5 or 10 beats). An intermittent inflow and outflow to side ports can be used to create an agitation-type effect and decrease the risk of thrombus formation. In some cases, a pump can require continuous irrigation.

A direct current charge can be used to prevent thrombus formation on an implanted assist device. For example, the device can be coated with a dielectric and can be configured to distribute a charge as described elsewhere (e.g., WIPO Patent Application WO/2008/02471). In some cases, the battery source that powers the pump can power side ports to produce a very low flow circulation on the surface of the tubing, wiring, and pump itself. In some cases, a second pump can be used to circulate blood along the left sided course of a primary assist device to reduce the risk of thrombus formation.

A pump can be powered by any appropriate power supply used with implanted devices (e.g., batteries/power source in the pump, or batteries positioned in the peripheral venous system, the infra-pectoral region, or other regions utilized in percutaneous techniques). In some cases, a pump can share a power supply with another implantable device.

Figure 3:
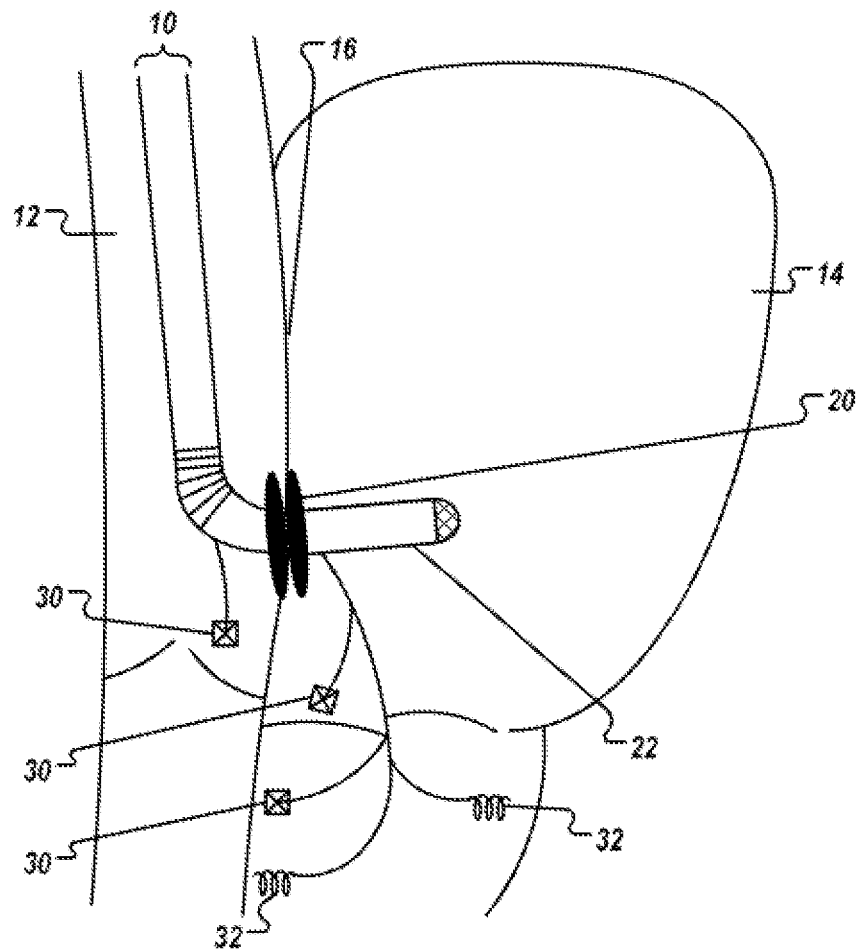
FIG. 3 shows an assist device including sensing and pacing electrodes positioned in a heart.

Referring to FIG. 3, a pump can be configured to alter blood flow in response to external stimuli. For example, a pump can be adapted to receive signals from sensing electrodes 30 capable of detecting atrial and ventricular function. In some cases, a pump can be adapted to receive input from a micro electro-mechanical sensor (e.g., a multi-axis accelerometer) or series of single-axis sensors that measure changes in body position. For example, rapid changes in body position (e.g., syncope) would activate the pump, or increase pump activity, to maintain perfusion during changes in body position. In some cases, a pump can be adapted to coordinate with cardiac function using pacing electrodes 32 and timing algorithms. A pump can be capable of receiving signals from sensing electrodes, and/or be capable of responding to a cardiac event. For example, a pump can deliver an electrical shock in response to an arrhythmia (e.g., to the left ventricle).

In some cases, sensing electrodes can be connected to an assist device to record changes in the electric potentials of specific cardiac loci. In some cases, a pressure sensor can be connected to an assist device. Sensing and pressure electrodes can permit real-time, online calculation of variations in heart rates and relative systolic and diastolic filling times to determine an algorithm that incorporates the timing of atrial signals at two different sites (e.g., to provide interatrial and intra-ventricular conduction times) and the pressure signals to assess electromechanical translation times. For example, the relative times between systole and diastole and heart rate can be predicted about 10 to 15 beats in advance. In some cases, a pump can be combined with pacing electrodes, to pace the heart according to timing algorithms determined by real-time calculations. To define heart rate further, the pump can be combined with pressure and sensing electrodes, and a QT sensor, impendence sensor, or accelerometer.

Figure 4:
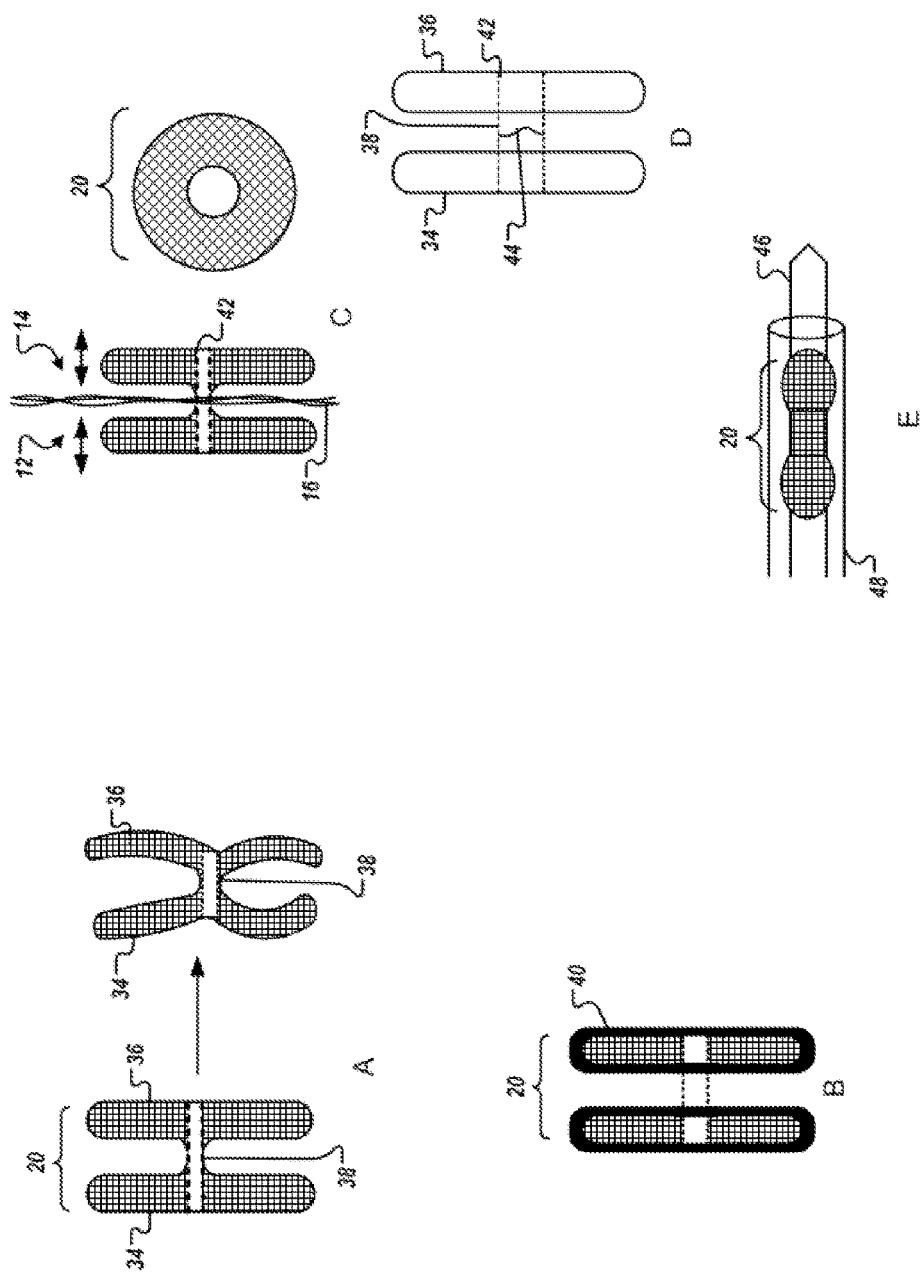
FIG. 4 depicts several examples of conduit designs that can be used in an assist device. Panel A shows a conduit with proximal and distal regions configured to secure a conduit to a wall in the cardiovascular system of a mammal. Panel B shows a conduit with covered proximal and distal regions. Panel C shows a conduit positioned in the shared wall between the left atrium and the aorta. Panel D shows a conduit with a tubular core featuring a septum. Panel E shows a conduit on a delivery dilator within a delivery sheath.

Referring to FIGS. 4A-E, an assist device can include a conduit 20 to provide access to two compartments of the cardiovascular system. A conduit can have a proximal region 34, a distal region 36, and an intermediate region 38 located between the proximal and distal regions. When viewed from either the proximal end or the distal end, the intermediate region of a conduit can define a lumen. The proximal and distal regions can be configured to secure a conduit within the cardiovascular system, for example, as shown in FIG. 4A. In some cases, the proximal and distal regions can include a covering 40, for example, as shown in FIG. 4B. The lumen defined by the intermediate region of the conduit can be supported by a tubular core 42, for example, as shown in FIG. 4C, which can include a septum or valve 44 as shown in FIG. 4D, for example. The dimensions of a conduit can be adapted to allow a needle or dilator 46 to pass through the intermediate region via the lumen, and then allow the conduit and needle to be inserted into a delivery sheath 48 for placement in the cardiovascular system, as shown in FIG. 4E, for example.

Any appropriate material can be used to construct a conduit or regions of a conduit. For example, a conduit can be constructed as one piece or multiple pieces (e.g., with separate proximal and distal regions). In some cases, a conduit can be constructed from compressible, expandable, or malleable materials (e.g., a balloon or shape-memory alloy (nickel titanium (nitinol)). For example, construction materials can permit the proximal and distal regions of a conduit to be deformed or compressed within the delivery sheath, but regain their original shape (e.g. lip, rim, or disk)

when the sheath is retracted. After positioning an expandable conduit, the expandable region can be filled with any suitable material for providing long-term stability (e.g., a polymer capable of crosslinking, thermosetting, or hardening). In some cases, a conduit can be constructed from magnetic or paramagnetic materials (e.g., to secure two close, but separate compartments of the cardiovascular system). Regions that are constructed from woven nitinol can be covered in a material for an atraumatic, fluid-tight seal (e.g., biocompatible polymers or fabrics). A tubular core can be constructed from any material that will support the intermediate region (e.g., polymer and/or metal). A septum or valve within a tubular core can be configured to prevent or control blood flow. In some cases, a septum can be adapted to be punctured to permit blood flow (e.g., upon pump placement).

The conduit size and shape can be adapted for the implantation site, method, or the anatomy of the recipient. In some cases, a conduit can be configured to be positioned between two chambers of a mammal's heart, between a chamber of the heart and a blood vessel, or within a blood vessel (e.g. to increase perfusion in the peripheral circulatory system). In some cases, a conduit can be configured for insertion in the shared wall between the aorta and the left atrium of a recipient. In some cases, a conduit can be configured to puncture the shared wall. The proximal and distal regions of a conduit can be adapted to fit securely against the site of implantation, while not fitting so tightly as to cause necrosis or other tissue damage. The proximal and distal regions of a conduit can be independently adjustable to be adapted to a specific recipient's anatomy as shown in FIG. 4A. In some cases, a conduit can be adapted to be secured to a tissue in a mammal (e.g., myocardium). The proximal and distal regions of a conduit can feature teeth or tines that can be twisted into the aortic valve, thereby securing the conduit, for example. In some cases, a conduit can be adapted to be secured using sutures.

Figure 5:
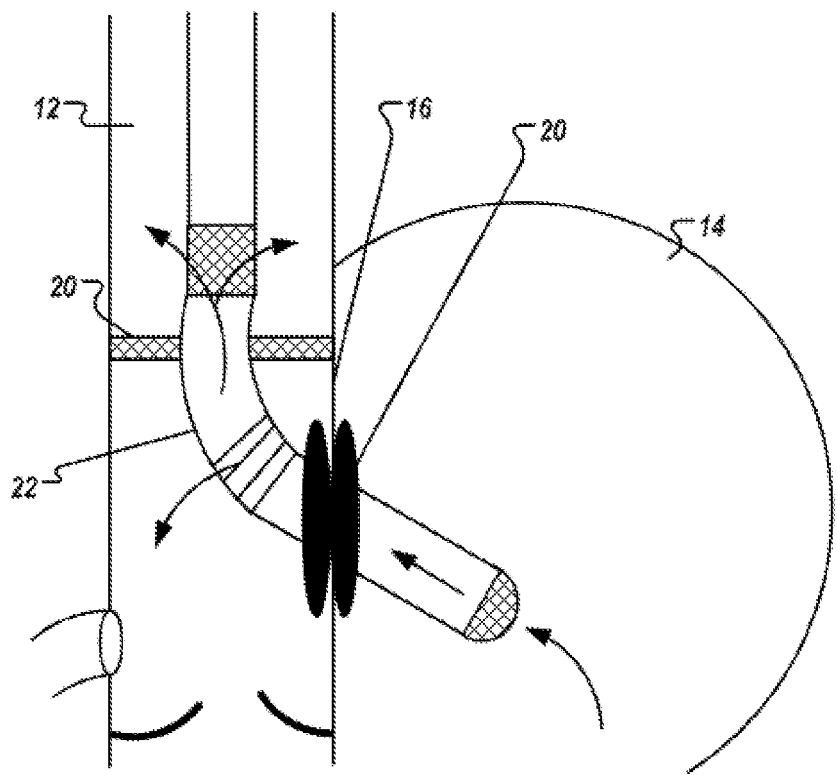
FIG. 5 shows an assist device featuring a conduit configured to enhance flow to the coronary arteries.

Referring to FIG. 5, an assist device can include more than one conduit 20 to control blood flow. For example, an assist device can include a second conduit to act as a valve or balloon-like device to be positioned in the aorta 12. Activation of balloon expansion or valve closure can be controlled by timing algorithms as described herein and/or by direct timing. This configuration can provide accentuated phasic systolic flow and greater diastolic filling into the coronary arteries. The position of the expandable conduit or valve can be variable. For example, a longer length can be used for recipients with a bypass graft. In some cases, the timing can be different from the timing of the native aortic valve. No prospective algorithms or pump design changes are required with this configuration because the flow rate is consistent.

Methods for implanting a percutaneous assist device in the cardiovascular system of a mammal are also provided herein. An assist device can be inserted into the cardiovascular system of a mammal using cardiac catheterization techniques (e.g., percutaneously). For example, a doctor can insert a delivery sheath into an artery or vein in a limb of a mammal. The sheath can be advanced into the chambers of the heart. A mammal can be any type of mammal including, without limitation, a mouse, rat, dog, cat, horse, sheep, goat, cow, pig, monkey, or human. A mammal can be identified as having a cardiovascular disease, such as congestive heart failure, valvular disease, or malignant arrhythmia using standard diagnostic techniques. In some cases, a mammal can have an artificial pacemaker or an implanted cardioverter-defibrillator.

Figure 6:
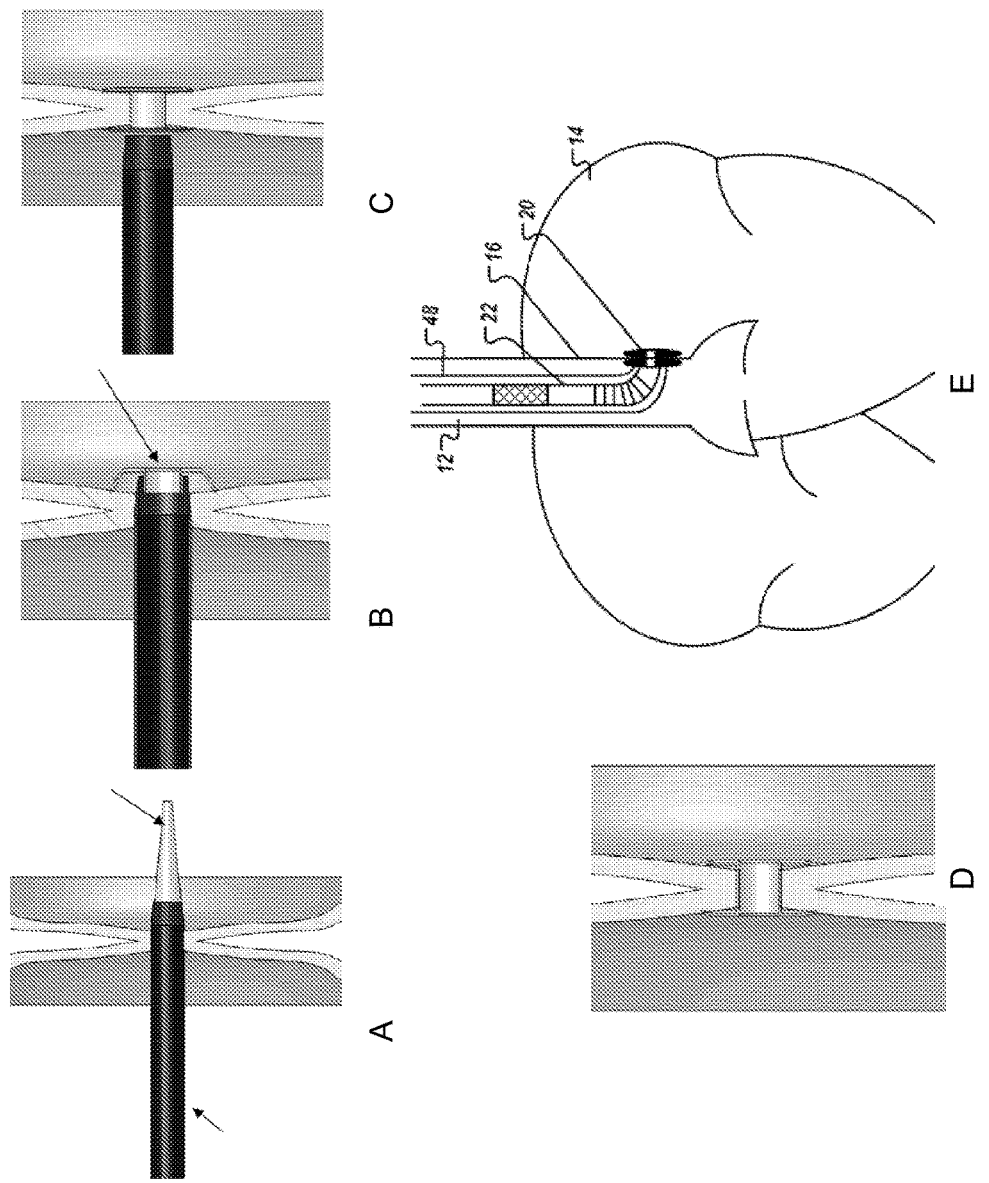
FIG. 6 is a diagram illustrating delivery of a conduit of an assist device. Panel A depicts a delivery dilator and delivery sheath accessing the left atrium via the aorta. Panel B shows the distal region of a conduit after exiting the delivery sheath. Panel C shows the proximal region of a conduit exiting the delivery sheath. Panel D shows a conduit connecting the aorta and left atrium. Panel E shows delivery of a pump via a delivery sheath.

Referring to FIG. 6A-E, a needle or dilator can be used to puncture a shared wall in the cardiovascular system to move a sheath into place across the shared wall (e.g., the wall between the non-coronary cusp of the aortic valve and the left atrium) as shown in FIG. 6A, for example. In some cases, puncturing can be accomplished using a radiofrequency energy/cautery or mechanical drill at the tip of the needle or dilator. A conduit can be advanced out of the sheath by moving the distal region out of the sheath for placement on the distal side of the wall (e.g., as shown in FIG. 6B), and then the sheath can be pulled back into the proximal side of the wall exposing the intermediate region of the conduit (e.g., as shown in FIG. 6C). The proximal region of the conduit can be advanced out of a sheath against the proximal wall (e.g., as shown in FIG. 6D). In some cases, a pump 22 can be advanced through a sheath 48 and through a conduit 20 in the shared wall 16 of the aorta 12 and left atrium 14 such that blood can be pumped from the left atrium into the aorta, for example, as shown in FIG. 6E.

Figure 7:
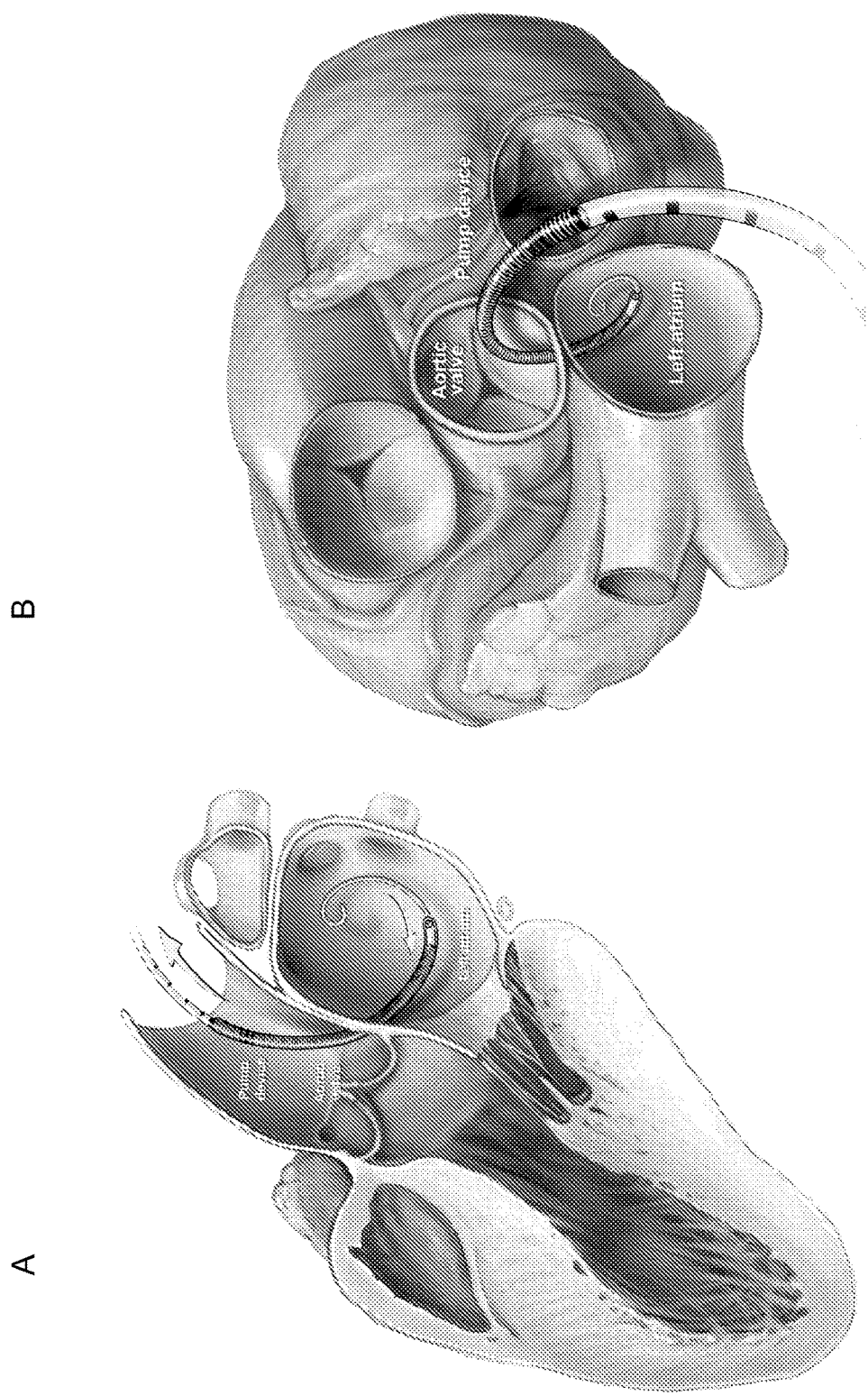
FIG. 7 is an illustration of a heart with an assist device positioned through the shared wall of the left atrium and the aorta. Panel A shows a cross-sectional side view. Panel B shows a top view.

In some cases, the left atrium is accessed in a retrograde fashion. For example, a needle can access the descending aorta and puncture the left atrium wall. After a conduit is positioned, a pump can be placed in the ascending aorta with the inflow in the left atrium (e.g., as shown in FIGS. 2 and 7). In some cases, any aortic cusp can be used to access the left atrium (e.g., the left coronary cusp or non-coronary cusp). For example, a conduit can be placed to permit communication between the posterior part of the left coronary cusp and the left atrium.

To aid in navigation of a puncturing device (e.g., a needle or wire) to the correct location between the aortic cusps and the left atrium, an electrogram guidance or other modality can be used. For example, when access to the left atrium is accomplished via the aorta (i.e., not the transseptal approach), electrodes can be positioned at the tip of the needle (and/or wire) and on the shaft. When advancing to the cusp, a large near-field ventricular electrogram can be obtained. In some cases, the electrogram can show that the needle or wire is above the valve plane, indicating that the needle or wire is pointing to the right coronary cusp; the surgeon would not advance that direction. For example, the surgeon can turn the needle or wire (if coming from the femoral) clockwise after withdrawing from the depths of the cusp until a large atrial electrogram and a far-field ventricular electrogram can be seen. The surgeon can advance the needle or wire into the noncoronary cusp. In some cases, before puncturing the shared wall, the timing of the local electrogram relative to the P wave (assuming sinus rhythm) can be checked. For example, an electrogram in the first 20 to 40% of the P wave can signify neighboring right atrium, and the needle or wire can puncture between the noncoronary cusp and the right atrium. If a local electrogram is in the terminal 40% of the P wave, the electrogram can indicate that the needle or wire is at the wall of the left atrium. In some cases, a very large atrial electrogram, which is not in the terminal 40%, can indicate that the needle or wire is adjacent to the interatrial septum. A surgeon can use the electrogram to turn the delivery catheter further counterclockwise, until the atrial electrogram becomes smaller (while remaining larger than the ventricular electrograms), indicating that the left atrium is neighboring. In some cases, a relatively equal atrial and ventricular electrogram with neither particularly near field can indicate that the needle or wire is in the left coronary cusp. From this position, a surgeon can withdraw the delivery catheter slightly and then turn or torque the delivery catheter clockwise to enter the noncoronary cusp. A surgeon can remain within the left coronary cusp, while avoiding the left main coronary artery, turn the needle or wire clockwise within the cusp, and then puncture from the left coronary cusp to the left atrium.

Figure 8:
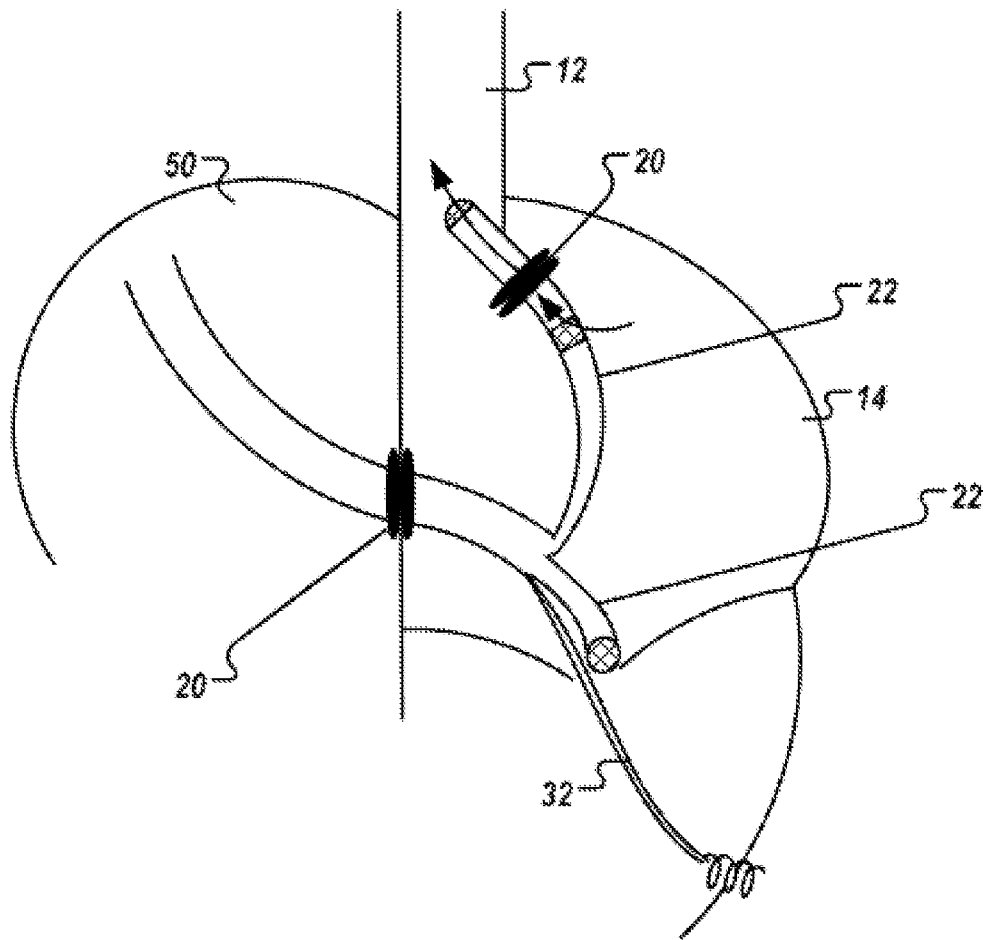
FIG. 8 shows a heart with multiple assist devices (e.g., a first device positioned across the atrial septum and a second device positioned across the shared wall of the aorta and the left atrium), with a pacing electrode located in the wall of the left ventricle, and a blocking element placed across the mitral valve.

Access to the ascending aorta posterior and the left atrium can be obtained through various approaches. As shown in FIG. 8, the ascending aorta posterior can be accessed through the right atrium 50 using a transseptal approach. For example, the right atrium can be accessed using a venous approach, and the left atrium 14 can be accessed by a transseptal puncture. The transseptal needle can be directed anteriorly to puncture from the left atrium into the ascending aorta 12. In some cases, the portion of the pump that bridges the Fossa Ovalis to the aorta can be adapted to prevent thrombus formation.

Figure 9:
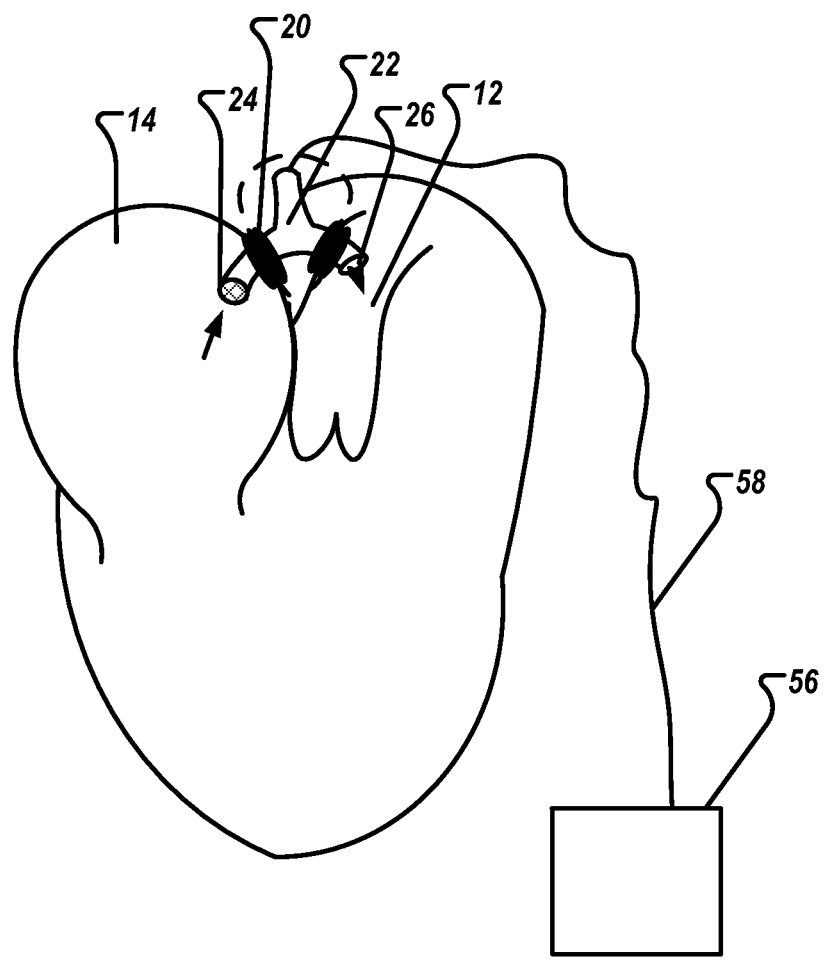
FIG. 9 shows epicardial implantation of an assist device.

Referring to FIG. 9, a left ventricular assist device can be positioned using an epicardial method. For example, the ascending aorta is the immediate anterior neighbor of the left atrium in the left part of the floor of the transverse sinus. After epicardial access is obtained, the transverse sinus can be cannulated. From the transverse sinus, a first conduit 20 can be positioned in the wall of left atrium 14, a second conduit can be positioned in the wall of the ascending aorta 12, and a pump 22 can be positioned through the first and second conduit to provide blood flow from the left atrium (e.g., via pump inflow 24) to the ascending aorta (e.g., via pump outflow 26). In some cases, a pump can be adapted to allow access to the left atrium and the ascending aorta (e.g., a bowed, Y-shaped, or V-shaped configuration). In some cases, a pump can be connected to a power source 56 by wire 58 (e.g., at the stem of the pump where pump inflow and outflow diverge). A power source 56 can be located in the abdomen or pericardial space, for example. In some cases, an epicardial placement of an assist device can be accomplished using the oblique sinus to connect left atrium to the descending aorta.

Figure 10:
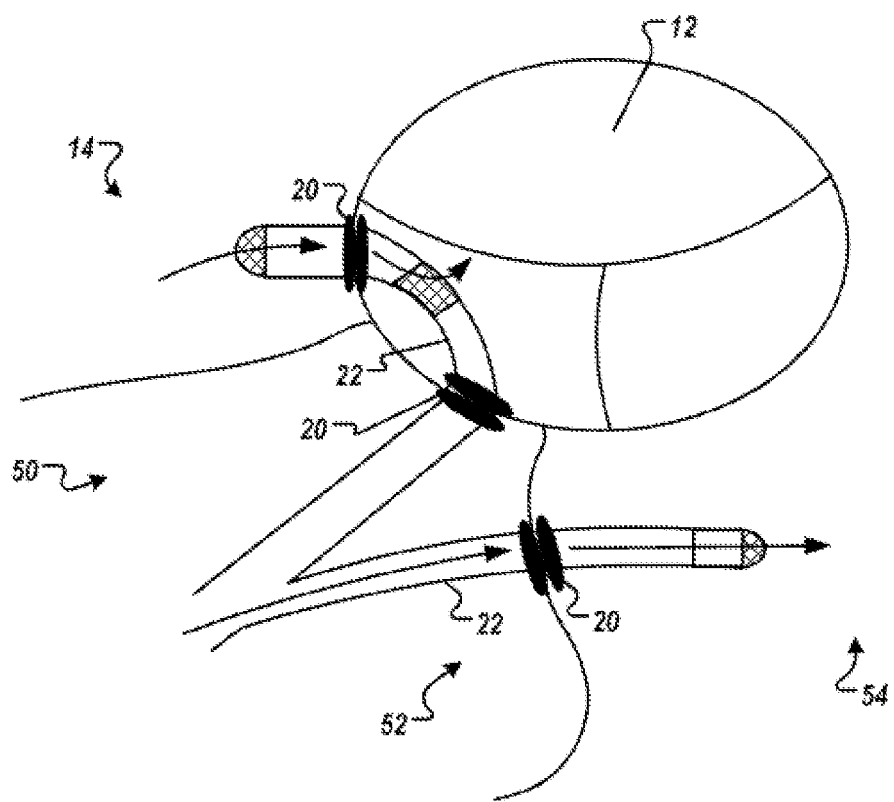
FIG. 10 shows multiple assist devices implanted to achieve a complete heart system.

Referring to FIG. 10, the non-coronary cusp of the ascending aorta can be accessed directly from the right atrium. For example, in this approach, the aorta 12 can be punctured from the right atrium 50 into the non-coronary cusp. The left atrium 14 can be punctured from the aorta 12. A pump 22 used for this approach can feature a generally circular shape (e.g., any configuration that permits perfusion from the right atrium, through the aortic valve, back to the left atrium, and then back to the right atrium across the septum). In some cases, pump 22 can be electrically synchronized with atria and ventricles.

In some cases, a combined approach can be used. For example, a retrograde aortic approach can be used to place the device, as described herein, and a transseptal route can be used to facilitate device placement. The aorta can be punctured with a small needle that takes a small wire (e.g., 0.027 wire) to provide radiographic visualization of the site of puncture in the left atrium. The wire can be snared from the left atrium and pulled into a sheath. In some cases, the wire can be pulled into a smaller sheath, and then the smaller sheath can be moved into a larger sheath. The sheath can be adapted with a needle or a bevel to puncture the left atrium wall to gain access to the aorta. In some cases, the sheath can be used to place the conduit into the aorta. The sheath can be pulled back into the left atrium to place the other end of the conduit. A pump can be positioned in the heart through the sheath and inserted into a conduit. The wire can enter the infrapectoral region (or other location), to secure an implanted assist device.

Multiple assist devices can be implanted into a mammal. In some cases, a complete heart system can be achieved by implanting several assist devices. See, e.g., U.S. Pat. No. 6,926,662. Referring to FIG. 10, one device can be placed in the aorta 12 and left atrium 14 using the transseptal approach described herein, and a second device can be placed into the pulmonary artery from the right atrial appendage 52. In some cases, the assist devices can be attached in series. In some cases, an assist device can be used in lieu of a Fontan procedure (e.g., to divert venous blood from the right atrium to the pulmonary arteries). For example, an assist device can be placed between the right atrial appendage (or other right atrial site) into the right ventricular outflow tract 54 or pulmonary artery. In some cases, an assist device can be positioned between the right atrial appendage and right ventricular outflow tract, the superior vena cava and pulmonary artery, or the right atrium and the pulmonary artery. In some cases, a right assist device and left assist device can include one or more electrodes. For example, electrodes on both the left-sided and right-sided pump can be electrically paired to allow simultaneous support of the right and left-sided circulation.

A space can exist between the left atrium and coronary cusp (e.g., in distal portions to the ascending aorta). To bridge this gap, the distal region of a conduit can be positioned in the aorta, and the proximal region can be placed in the left atrium in close apposition. In some cases, the conduit ends and the pump can be secured or stabilized by magnets. In some cases, tines or clasp devices can be used to bring separate walls into close apposition.

Figure 11:
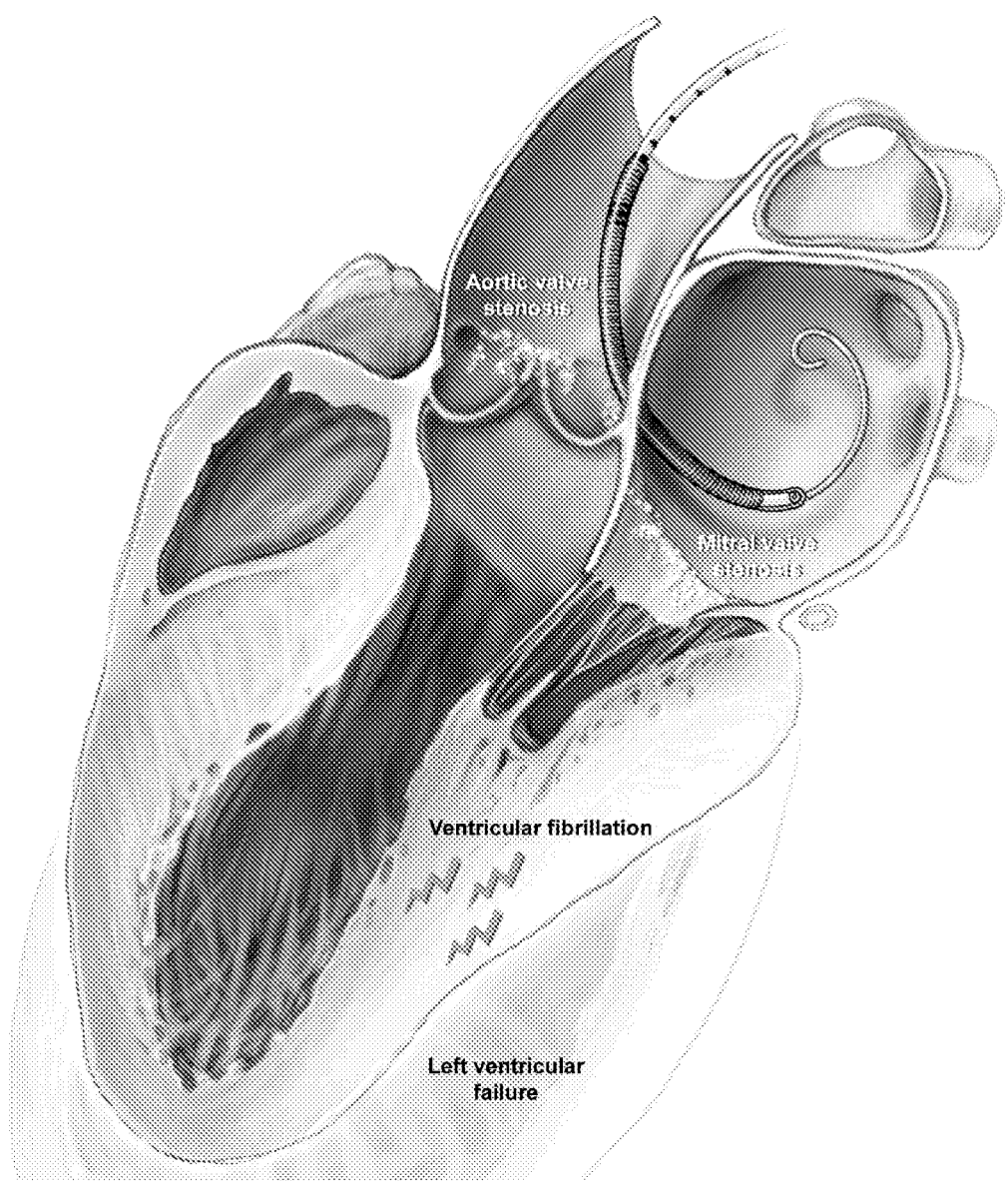
FIG. 11 is an illustration of a cross-section of a heart with pathological conditions and an assist device in place at the shared wall between the left atrium and the aorta.

This document also provides methods of treating cardiovascular diseases using an assist device. For example, a percutaneous assist device can be used to treat congestive heart failure, ventricular fibrillation, aortic or mitral valve stenosis, syncope (as seen in structural heart disease) and other heart diseases or conditions that impair blood flow (e.g., as shown in FIG. 11). In addition, this document provides methods of treating cardiovascular diseases using assist devices in series. For example, an assist device positioned between the left atrium and the ascending aorta can be connected in series to a second assist device placed between the right atrial appendage and the right ventricular outflow tract, the superior vena cava and the pulmonary artery, or the right atrium and the pulmonary artery. In some cases, assist devices in series can be used to treat patients with severe right ventricular failure concomitant with left ventricular failure, patients with congenital heart disease including tricuspid atresia, pulmonary atresia, or right ventricular hypoplasia, or patients with severe right ventricular arrhythmogenic cardiomyopathy, Uhl's anomaly or similar disease states.

To prevent aortic regurgitation, a pump can be placed across the aortic valve through a transseptal, prograde, or antegrade route to enhance blood flow from the left ventricle to the aorta. An expandable balloon, which can be configured to prevent aortic regurgitation due to the presence of the pump across the aorta, can be positioned above the aortic valve. An expandable conduit can be filled with any appropriate substance to prevent regurgitation above the aortic valve (e.g., polymers that can be cross-linked using thermal or radio frequency energy, heat-denatured polymers, fibrinogen-based polymers, or thermosetting epoxide polymers). The pump can be configured to permit coronary perfusion via side holes that allow blood to pass between the aorta valve and the occlusion balloon. In some cases, a balloon can be placed above the aortic valve (e.g., in patients who have underlying aortic regurgitation (as shown in FIG. 7, for example)). The balloon can be secured to the wall of the aorta itself. In some cases, the balloon can be inflated. An expandable conduit with a tubular core can be inflated intermittently to serve as a counter pulsation device.

In some cases, an assist device can be used to treat ventricular tachycardia, atrial fibrillation, and symptomatic patients (e.g., patients with severe diastolic dysfunction) who do not have congestive heart failure or critical valvular disease. The pump can be configured to begin pumping when an arrhythmia, ventricular fibrillation, or a rapid ventricular tachycardia is detected. In some cases, a right ventricular assist device and a left ventricular assist device can be implanted. When an arrhythmia is detected, the left ventricular assist device can be turned on. If the patient remains symptomatic, the activity of the right ventricular assist device can be triggered. In some cases, the power of the second pump can be controlled externally (e.g., with a magnet or other external applicator).

The pump can be configured to respond to electrodes positioned to detect ventricular fibrillation or rapid ventricular tachycardia (e.g., as shown in FIG. 3)). For example, an electrode can be extended from the assist device to the left ventricle. In some cases, an electrode can extend from the connection to the battery source into the right ventricle. A far-field electrode can be included. For example, one electrode can be placed at the tip of the pump (i.e., above the aortic valve) and another electrode can be in the power supply of the pump. In some cases, a second electrode can be prolapsed into the right ventricle or left ventricle.

An assist device can provide support to a patient with an implanted cardioverter-defibrillator (ICD). For example, the sensing components of an ICD (and/or the control/power unit of the ICD) can be shared by a pump. In some cases, an assist device can be implanted in an ICD patient to provide support during an arrhythmia. For example, symptoms of an arrhythmia can be minimized with a pump output of approximately 3 liters/minute and provide time for the patient to proceed to a hospital for sedation, defibrillation, or more invasive procedures.

To treat diastolic dysfunction, an assist device can be used to off-load the left atrium and improve left atrial pressures, pulmonary venous pressures, pulmonary capillary wedge pressures, and diastolic ventricular function. Configurations to off-load the left atrium to the right atrial circulation can augment the ability of an assist device to prevent pulmonary edema and improve diastolic function. For example, incorporating sinus rhythm into the timing algorithm can cause left atrial to left ventricular (or aortic) filling to occur prior to the natural ventricular outflow. This period can be about equal to the atrioventricular interval. The atrial contribution to cardiac output can be directed to the aorta and can be synchronized with a pump. These methods can be combined with an agitation or reverse pumping function as described herein.

In some cases, patients with critical stenotic valvular disease or with some forms of severe regurgitant valvular disease can display inadequate forward flow to the systemic circulation and excessive "backward" flow resulting in pulmonary edema. An assist device can be used as a valve through the left atrial wall and the non-coronary cusp to enhance forward flow (e.g., as shown in FIG. 5).

Critical mitral valve disease, tricuspid disease, or pulmonary valve disease can also be treated. For example, off loading of the left atrium can improve the hemodynamics of mitral regurgitation. The regurgitant jet can be directed into the aorta to enhance the natural forward flow by positioning a pump inflow at the mitral valve (e.g., as shown in FIG. 7). The pump inflow can avoid blocking the mitral annulus to maintain diastolic filling.

An assist device can be combined with a valve-like structure. For example, an assist device can be deployed using a transseptal or trans-aortic approach, as described herein. An inflow port can be placed on the mitral annulus such that the mitral regurgitant jet takes blood to the aorta. A valve can be placed on the superior-convexity-leftward portion such that when mitral regurgitation occurs the valve closes and the blood flows to the aorta. In the absence of mitral regurgitation, inflow proceeds to the ventricle. The pump can accentuate inflow to the ventricle and outflow to the aorta, as needed.

In some cases, assist devices described herein can be used for perfusion or for treatment of small vessel coronary disease (e.g., as a "stent-pump"). For example, an outflow port can be placed in the proximal aortic root (e.g., as shown in FIG. 5). An inflatable conduit can be positioned at the supravalvar cusp to increase pressure in the proximal aorta and perfuse the coronary artery. A cannula can be used to engage in coronary arteries such that left atrial blood is "pumped" into the coronary artery.

Direct cannulation of the coronary arteries can be achieved using an assist device as a stand-alone pump. A battery source can be contained within the pump, in the infra-pectoral region, or other regions utilized in percutaneous techniques. The pump can be implanted in the coronary arteries as described for a stent. The power can be supplied with a battery placed within or near the stent, via a wire and battery source, or through an external source.

Treatment of peripheral vascular disease can be achieved with an assist device with an active pump or as a stand-alone device (a "pump-stent") in any peripheral vascular bed (e.g., the vascular bed of the brain, lower extremities, or upper extremities.). For example, a pump stent can cannulate a vessel such as a carotid artery or femoral artery. The stand-alone pump-stent can be used to increase perfusion pressure for the treatment of vascular and vascular bed disease (e.g., small vessel coronary disease, small vessel peripheral arterial disease, or small vessel central nervous system disease). A pump-stent can be powered by a battery located within the stent. In some cases, a battery source can be contained outside of the vessel in which the assist device is implanted (e.g., a subcutaneously implanted power supply). A distal vessel or a vessel close to the implant can be a point of entry for connecting a battery source to a "pump-stent" (e.g., femoral artery or subclavian artery).

In some cases, an assist device can be used in combination with other cardiac technology. For example, an assist device can function as a defibrillator, or can have wires that can be used for pacing of the cardiac chambers. The device can serve an adjunctive role. For example, a pump can be triggered by a ventricular arrhythmia, as described herein. During the activation time, anti-tachycardia pacing can be attempted repeatedly without a risk syncope or sudden death. Prolonged anti-tachycardia pacing attempts can allow for conversion to normal rhythm. Similarly, an assist device can be activated to deliver a shock after the patient has been sedated and evaluated by a health care provider. A shock can be delivered via coils that are screwed in or imbedded into myocardium and serve as a multi-coil defibrillator. Coils can serve as electrodes to help time the pump (e.g., by multi-site ventricular stimulation and multi-site sensing).

The invention will be further described in the following examples, which do not limit the scope of the invention described in the claims.

EXAMPLES

Example 1—Continuity of Septum Between Left Atrium and Ascending Aorta

The anatomies of 40 autopsied human hearts were studied. A continuity of the septum between the left atrium and the ascending aorta posterior (in the region of the non-coronary cusp) was present in all 40 hearts. The average area of this continuity was 9.6 mm×5.6 mm (length×width). Thus, this region of the heart can be used to position an assist device to enhance blood flow from the left atrium to the aorta.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating heart disease in a mammal using an assist device comprising (i) a conduit comprising a proximal region, a distal region and an intermediate region located between said proximal and distal regions, wherein said proximal region is adapted to be positioned within an aorta of said mammal, wherein said distal region is adapted to be positioned within a left atrium of said mammal, and wherein said intermediate region is adapted to define a lumen through a shared wall between said aorta and said left atrium, and (ii) a pump, wherein said pump is adapted to be positioned within said conduit,
wherein said method comprises implanting said assist device with said proximal region positioned within said aorta, said distal region positioned within said left atrium, and said intermediate region positioned to extend from said aorta to said left atrium across said shared wall between said aorta and said left atrium without being positioned outside of said aorta, said left atrium, and said shared wall, wherein said shared wall extends along the ascending aorta to the aortic valve,
wherein blood flow in said mammal is enhanced, thereby treating said heart disease.

2. The method of claim 1, wherein said method comprises identifying said mammal as having a heart disease selected from the group consisting of congestive heart failure, valvular disease, and malignant cardiac arrhythmia.

3. The method of claim 1, wherein said mammal is a human.

4. The method of claim 1, wherein said conduit is constructed of expandable or malleable material.

5. The method of claim 4, wherein said malleable material is nitinol.

6. The method of claim 1, wherein said proximal region and said distal region are independently adjustable.

7. The method of claim 1, wherein said intermediate region comprises a tubular core.

8. The method of claim 7, wherein said tubular core comprises a septum or valve.

9. The method of claim 1, wherein said ventricular assist device comprises electrodes.

10. A method for implanting an assist device into a human, wherein said method comprises (i) inserting a conduit having a proximal region, a distal region, and an intermediate region located between said proximal and distal regions into a position wherein said proximal region is located within the aorta of said human, said distal region is located within the left atrium of said human, and said intermediate region defines a lumen through the shared wall between said aorta and left atrium without being positioned outside of said aorta, said left atrium, and said shared wall, wherein said shared wall extends along the ascending aorta to the aortic valve, and (ii) inserting a pump into said conduit such that blood is pumped through said conduit from said left atrium to said aorta.

11. The method of claim 10, wherein said conduit is constructed of expandable or malleable material.

12. The method of claim 11, wherein said malleable material is nitinol.

13. The method of claim 10, wherein said proximal region and said distal region are independently adjustable.

14. The method of claim 10, wherein said intermediate region comprises a tubular core.

15. The method of claim 14, wherein said tubular core comprises a septum or valve.

16. The method of claim 10, wherein said ventricular assist device comprises electrodes.

17. A method for treating heart disease in a mammal using an assist device comprising (i) a conduit comprising a proximal region, a distal region and an intermediate region located between said proximal and distal regions, wherein said proximal region is adapted to be positioned within an aorta of said mammal, wherein said distal region is adapted to be positioned within a left atrium of said mammal, and wherein said intermediate region is adapted to define a lumen through a shared wall between said aorta and said left atrium, and (ii) a pump, wherein said pump is adapted to be positioned within said conduit,
wherein said method comprises implanting said assist device with said proximal region positioned within said aorta, said distal region positioned within said left atrium, and said intermediate region positioned to extend from said aorta to said left atrium through a piercing of said shared wall between said aorta and said left atrium without being positioned outside of said aorta, said left atrium, and said shared wall,
wherein blood flow in said mammal is enhanced, thereby treating said heart disease.

18. The method of claim 17, wherein said method comprises identifying said mammal as having a heart disease selected from the group consisting of congestive heart failure, valvular disease, and malignant cardiac arrhythmia.

19. The method of claim 17, wherein said mammal is a human.

20. The method of claim 17, wherein said conduit is constructed of expandable or malleable material.

21. The method of claim 20, wherein said malleable material is nitinol.

22. The method of claim 17, wherein said proximal region and said distal region are independently adjustable.

23. The method of claim 17, wherein said intermediate region comprises a tubular core.

24. The method of claim 23, wherein said tubular core comprises a septum or valve.

25. The method of claim 17, wherein said ventricular assist device comprises electrodes.

26. A method for implanting an assist device into a human, wherein said method comprises (i) inserting a conduit having a proximal region, a distal region, and an intermediate region located between said proximal and distal regions into a position wherein said proximal region is located within the aorta of said human, said distal region is located within the left atrium of said human, and said intermediate region extends through a piercing of a shared wall between said aorta and left atrium without being positioned outside of said aorta, said left atrium, and said shared wall, and (ii) inserting a pump into said conduit such that blood is pumped through said conduit from said left atrium to said aorta.

27. The method of claim 26, wherein said conduit is constructed of expandable or malleable material.

28. The method of claim 27, wherein said malleable material is nitinol.

29. The method of claim 26, wherein said proximal region and said distal region are independently adjustable.

30. The method of claim 26, wherein said intermediate region comprises a tubular core.

31. The method of claim 30, wherein said tubular core comprises a septum or valve.

32. The method of claim 26, wherein said ventricular assist device comprises electrodes.

\* \* \* \* \*